United States Patent [19]

Konishi et al.

[11] 4,341,768

[45] Jul. 27, 1982

[54] ANTIBIOTIC COMPOUNDS

[75] Inventors: Masataka Konishi; Takeo Miyaki, both of Yokohama; Hiroshi Tsukiura, Tokyo; Hiroshi Kawaguchi, Tokyo, all of Japan

[73] Assignee: Bristol-Myers Company, New York, N.Y.

[21] Appl. No.: 250,987

[22] Filed: Apr. 3, 1981

[51] Int. Cl.[3] .................... A61K 37/00; C07C 103/52; A61K 35/00

[52] U.S. Cl. ............................ 424/177; 260/112.5 R; 424/119

[58] Field of Search .............................. 424/119, 177; 260/112.5 R

[56] References Cited

U.S. PATENT DOCUMENTS 3,856,938 12/1974 Murao et al. ...................... 424/119
3,880,944 4/1975 Kawaguchi et al. .............. 424/119

OTHER PUBLICATIONS

Biol. Abstr. (67) 59991; 59994; 59995, (63) 19114 and (69) 71255.
The Journal of Antibiotics 29, (1976), 516–519 and 1339–1340 and 1241–1242.
Journal of Chromatography 97 (1974), 112–114.
The Journal of Antibiotics (1973), 444–448, vol. 26.
The Journal of Antibiotics (28), 379–389, (1975).
Japanese Abstract (1974), 160491.

*Primary Examiner*—Delbert R. Phillips
*Attorney, Agent, or Firm*—David M. Morse

[57] ABSTRACT

A novel peptide antibiotic complex designated herein as Bu-2470 is produced by fermentation of *Bacillus circulans* strain G493-B6 (ATCC 31,805). Complex Bu-2470 may be separated into four bioactive peptide antibiotics designated as Bu-2470A, $B_1$, $B_{2a}$, and $B_{2b}$. The complex and individual bioactive factors possess significant antimicrobial activity.

14 Claims, 6 Drawing Figures

WAVELENGTH
WAVE NUMBER (cm⁻¹)
PERCENT TRANSMISSION

WAVELENGTH
WAVE NUMBER (cm⁻¹)
PERCENT TRANSMISSION

WAVELENGTH
2.5
3
4
5
6
7
8
9
10
11
12
13
14
15
WAVE NUMBER (cm⁻¹)
4000
3600
3200
2800
2400
2000
1800
1600
1400
1200
1000
800
650
PERCENT TRANSMISSION
100
80
60
40
20
0

0
1
2
3
4
5
6
7
8
9
ppm

ANTIBIOTIC COMPOUNDS

BACKGROUND OF THE INVENTION

1. Field of the Invention

This invention relates to a new peptide antibiotic complex and to its production, recovery and separation into four bioactive antibiotic components.

2. Description of the Prior Art

The Bu-2470 antibiotic complex of the present invention comprises a mixture of co-produced individual antibiotic factors. Of the four major bioactive factors, one is a non-acylated octapeptide antibiotic and three are octapeptide antibiotics acylated with a fatty acid residue. The new antibiotics are produced by fermentation of a new strain of Bacillus designated *Bacillus circulans* strain G493-B6 (ATCC 31,805).

Several acylated octapeptide antibiotics have been described in the literature. Those produced by fermentation of *Bacillus circulans* strains include the following:

1. Antibiotic Bu-1880 disclosed in U.S. Pat. No. 3,880,994 is an octapeptide acylated with a 3-hydroxy-8-methyldecanoic acid fatty acid residue. Bu-1880 is produced by fermentation of *Bacillus circulans* ATCC 21828 and contains the amino acids phenylalanine, leucine and $\alpha,\gamma$-diaminobutyric acid in a ratio of 1:2:5. While the structure of Bu-1880 has not yet been determined, Bu-1880 can be clearly differentiated from antibiotic components Bu-2470 A, $B_{2a}$ and $B_{2b}$ on the basis of its physicochemical properties and fatty acid moiety.

2. Japanese Published Patent Application No. 50/160,491 discloses the acylated octapeptide antibiotic 333-25 produced by fermentation of *Bacillus circulans* No. 333-25 (FERM-P2362) (see also *J. Antibiotics* 29:516–520, 1976). Antibiotic 333-25 is described in *J. Antibiotics* 29 (12): 1339–1340 (1976) as having the structure

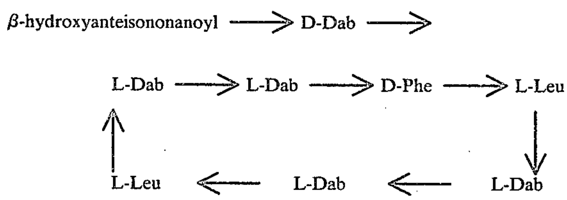

wherein Dab is $\alpha,\gamma$-diaminobutyric acid, Phe is phenylalanine and Leu is leucine. The 333-25 antibiotic can be differentiated from the antibiotics of the present invention by the presence of the $\beta$-hydroxy anteisononanoyl fatty acid moiety.

3. The antibiotic complex EM-49 is disclosed in U.S. Pat. No. 3,856,938 as being produced by fermentation of *Bacillus circulans* ATCC 21656. The complex consists of four major components, $\alpha,\beta,\gamma$ and $\delta$. which are cyclic octapeptides monoacylated with $\beta$-hydroxy fatty acids. The four components are distinguishable by their amino acid compositions and variations in the structure of their fatty acid moieties. EM-49 $\alpha$ and $\beta$ contain no phenylalanine, five residues of 2,4-diaminobutyric acid and three residues of leucine. EM-49 $\gamma$ and $\delta$ contain one residue of phenylalanine, two residues of leucine and five residues of 2,4-diaminobutyric acid. EM-49 $\alpha$ and $\beta$ differ from each other in the structures of the fatty acid moieties. EM-49 $\gamma$ and $\delta$ differ from each other in the same way. [see also *J. Chromatography* 97:112–114 (1974) and *J. Antibiotics* 26:444–448 (1973)].

From *J. Antibiotics* 28:379–389 (1975) and *J. Antibiotics* 29:1241–1242 (1976), the structures of the EM-49 antibiotics (including further subfactors of $\alpha$ and $\gamma$ may be represented as follows:

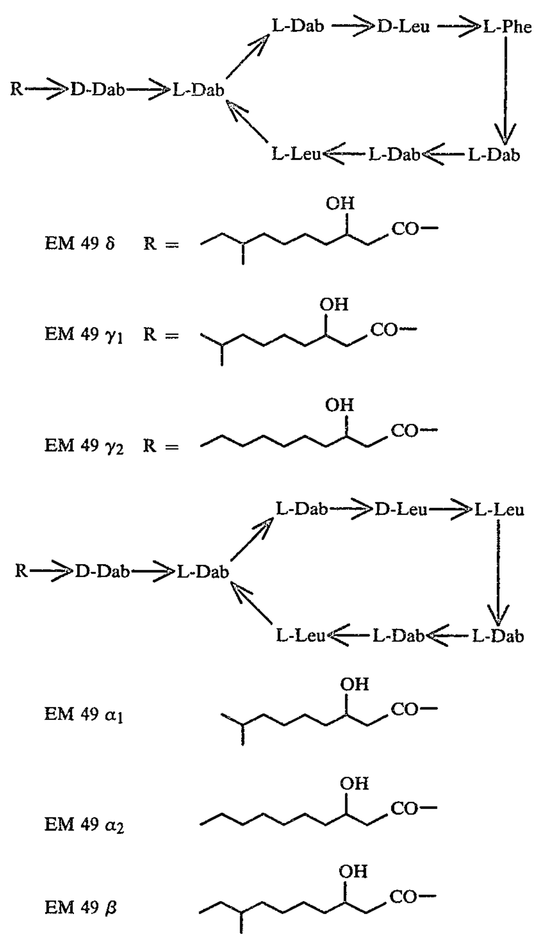

The EM-49 antibiotics differ from the compounds of the present invention in their amino acid compositions.

The antibiotic Y-8495 produced by fermentation of *Bacillus bungoensis* (FERM-P 2143) is disclosed in Japanese Published Patent Application No. 50/25,795. Y-8495 is an octapeptide antibiotic, but it can be differentiated from the compounds of the present invention on the basis of its physicochemical properties.

SUMMARY OF THE INVENTION

There is provided by the present invention a new complex of basic peptide antibiotics designated Bu-2470, said complex being produced by cultivating a new strain of *Bacillus circulans* designated *Bacillus circulans* strain G493-B6 (ATCC 31,805), or variants or mutants thereof, in an aqueous nutrient medium containing assimilable sources of carbon and nitrogen under submerged aerobic conditions until a substantial amount of Bu-2470 complex is produced by said organism in said culture medium and, subsequently, recovering the Bu-2470 complex from the culture medium. The invention also provides procedures for providing the four bioactive factors of Bu-2470 designated Bu-2470A, $B_1$, $B_{2a}$ and $B_{2b}$ as individual peptide antibiotics substantially free of co-produced substances. Bu-2470 complex and the individual peptide antibiotic factors may be obtained either as free bases or as pharmaceutically acceptable acid addition salts thereof.

DETAILED DESCRIPTION

Figure 1:
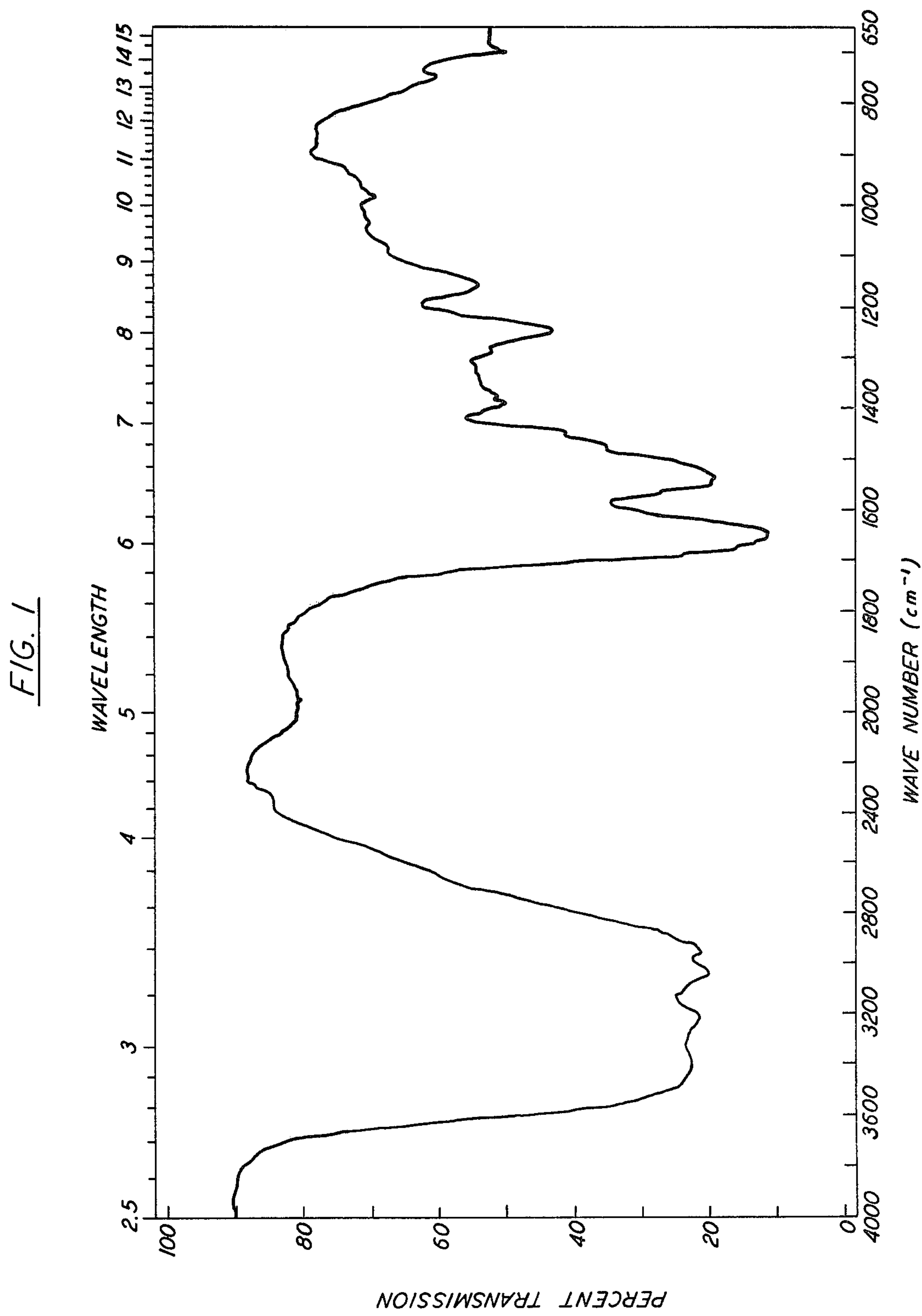
FIG. 1 shows the infrared absorption spectrum of Bu-2470A hydrochloride when pelleted in potassium bromide.

This invention relates to a novel complex of basic peptide antibiotics designated herein as Bu-2470 and to its preparation by fermentation of a new strain of Bacillus designated *Bacillus circulans* strain G493-B6. The producing organism is an aerobic, spore-forming rod bacterium isolated from a soil sample collected in India. A culture of this organism has been deposited in the American Type Culture Collection, Washington, D.C., and added to its permanent collection of microorganisms as ATCC 31,805.

Taxonomy of the Producing Organism

The morphological, cultural and physiological characteristics of strain G493-B6 are shown in Tables 1, 2 and 3, respectively.

TABLE 1

| Morphological Characteristics of Strain G493-B6 | |
|---|---|
| Vegetative cells | |
| Shape: | Rods. Rounded end. |
| Size: | 0.5∼0.7 × 2.0∼4.0μ |
| Motility: | Positive |
| Spores | |
| Shape and size: | Elliptical, 0.8 × 1.6μ |
| Distension of sporangia: | Swollen at spore site |
| Position: | Terminal or subterminal, rarely central |
| Gram-stain: | Negative |

TABLE 2

| Cultural Characteristics of Strain G493-B6 | |
|---|---|
| Sabouraud dextrose broth: | Poor growth. |
| Glucose peptone broth: | Turbid with viscous sediment. No pellicle. pH 5.5. |
| Nutrient agar slant: | Moderate growth. Thin, opaque, smooth, slightly viscous and creamy. |
| Colony on nutrient agar: | Circular or slightly irregular. Raised with irregular margin. Opaque density and smooth surface. 2∼4 mm in diameter. Slightly viscous and creamy white. No satellite colony. |

(Incubation at 37° C. for 24 hr.)

TABLE 3

| Physiological Characteristics of Strain G493-B6 | |
|---|---|
| Temperature for growth | |
| Growth: | 20∼45° C. |
| No Growth: | 10° C. and 50° C. |
| Gas from glucose, arabinose, xylose or mannitol: | Negative |
| Acid from arabinose, xylose or mannitol: | Positive |
| Acetoin from glucose: | Negative |
| Hydrolysis of starch: | Positive |
| Indole production: | Negative |
| Nitrite from nitrate: | Positive |
| Liquefaction of gelatin: | Positive |
| Catalase: | Positive |
| Deamination of phenylalanine: | Negative |
| Growth in 0.001% lysozyme: | Positive |
| Growth on anaerobic agar: (Hugh-Leifson medium) | Positive |
| Citrate utilization: | Positive |
| Reaction in milk: | Peptonized and coagulated |
| Decomposition of urea: | Positive |
| NaCl tolerance: | Growth at 3%, and no growth at 4% |

From the above, it can be seen that *Bacillus circulans* strain G493-B6 has the following diagnostic characteristics: (1) negative gram-stain; (2) sporangia swollen at the endospore site; (3) spores formed at terminal or subterminal sites; (4) elliptical spores; (5) acid but no gas produced from glucose, arabinose, xylose or mannitol; (6) starch is hydrolyzed; (7) acetoin is not produced; (8) indole is not produced; and (9) moderate growth occurs in ordinary media such as nutrient agar. From the above characteristics, the organism was classified as belonging to the genus Bacillus.

Among the 22 species of the genus Bacillus described in *Bergey's Manual* (8th Ed., 1974), 5 species do not grow in ordinary media and thus can be differentiated from strain G493-B6. Of the remaining 17 species, 8 species (*B. alvei, B. brevis, B. circulans, B. coagulans, B. laterosporus, B. macerans, B. polymyxa* and *B. stearothermophilus*) have some morphological similarity to the producing strain. Therefore, strain G493-B6 was compared with each of the eight species. The microbiological characteristics of strain G493-B6 are very similar to those of *B. circulans*. However, strain G493-B6 differs from *B. polymyxa* and *B. macerans* in its ability to evoke gas production from glucose; from *B. stearothermophilus* and *B. coagulans* in its sporangia distension at the endospore site and its lack of growth at 50° C.; from *B. alvei* in its formation of acid from arabinose, xylose or mannitol and its lack of indole production; and from *B. laterosporus* and *B. brevis* in its formation of acid from arabinose or xylose and its hydrolysis of starch. Accordingly, the producing organism was determined to be a strain of *Bacillus circulans*.

As in the case with other organisms, the characteristics of strain G493-B6 are subject to variation. For example, artificial variants and mutants of the G493-B6 strain may be obtained by treatment with various known mutagens such as ultraviolet rays, x-rays, high frequency waves, radioactive rays and chemicals. All natural and artificial variants and mutants (hereinafter referred to as mutants) of *Bacillus circulans* G493-B6 which produce the Bu-2470 antibiotics are intended to be included within the scope of the present invention.

Antibiotic Production

Antibiotic complex Bu-2470 is produced by cultivating a Bu-2470-producing strain of *Bacillus circulans*, most preferably the strain *Bacillus circulans* strain G493-B6 having the identifying characteristics of ATCC 31,805, or a mutant thereof, under submerged aerobic conditions in an aqueous nutrient medium. The organism is grown in a nutrient medium containing an assimilable carbon source, for example an assimilable carbohydrate. Examples of suitable carbon sources include glucose, ribose, galactose, fructose, mannose, sucrose, lactose, soluble starch and glycerol. The nutrient medium should also contain an assimilable nitrogen source such as, for example, fish meal, soybean meal, corn steep liquor, peptones, meat extract, peanut flour, yeast extract or ammonium salts. Inorganic salts such as sodium chloride, potassium chloride, magnesium sulfate, calcium carbonate, phosphates, etc. are added if necessary. Trace elements such as copper, manganese, iron, zinc, etc. are added to the medium if desired or may be supplied as impurities of other constituents of the media. The incubation temperature may be any temperature at which a Bu-2470-producing strain is able to grow, e.g. 20°-45° C., but it is preferable to conduct the fermentation at 25°-35° C., especially 27°-32° C. A neutral or near neutral initial pH, e.g. pH$\sim$6-7, is preferably employed in the medium and production of antibiotic is generally carried out for a period of from about 2 to 7 days. Ordinarily, optimum production is achieved in 4 to 6 days. For preparation of relatively small amounts, shake flasks and surface culture can be employed, but for the preparation of larger amounts, submerged aerobic culture in sterile tanks is preferred. When tank fermentation is to be carried out, it is desirable to produce a vegetative inoculum in a nutrient broth by inoculating the broth culture with a spore from the organism and, when a young active vegetative inoculum has been obtained, transferring the inoculum aseptically to the fermentation tank medium. Aeration in tanks and bottles may be provided by forcing sterile air through or onto the surface of the fermenting medium. Further agitation may be provided by a mechanical impeller. Antifoaming agents such as lard oil may also be added if needed.

The production of Bu-2470 in the fermentation medium can readily be followed during the course of fermentation by the paper disc-agar diffusion assay using *Bacillus subtilis* PCI 219 and *E. coli* NIHJ as test organisms.

Isolation of the Bu-2470 Antibiotics

After optimum broth potency has been obtained, the mycelium and undissolved residues are separated from the fermentation broth by conventional means such as filtration or centrifugation. The antibiotic activity is contained in the supernatant (or filtrate) and may be recovered therefrom by employing conventional methods for isolation of basic antibiotics such as solvent extraction and adsorption techniques.

To illustrate one procedure for isolating the individual antibiotic factors of the present invention, the supernatant or filtrate (after removal of mycelial cake) may be adsorbed onto a cationic exchange resin such as AMBERLITE IRC-50 and the resin then eluted with a mineral acid solution to liberate the Bu-2470 antibiotics. The eluate is next neutralized and adsorbed onto activated charcoal. The adsorbed antibiotics are eluted from the charcoal with, for example, aqueous n-butanol at acid pH. The butanol layer is separated and lyophilized or concentrated in vacuo to give a mixture of the Bu-2470B components ($B_1$, $B_{2a}$ and $B_{2b}$). The acidic aqueous layer is neutralized and then extracted with n-butanol to give, upon evaporation of the n-butanol extract, additional Bu-2470B components. The aqueous layer from the neutral n-butanol extraction may be basified (e.g. pH 10) and extracted again with n-butanol to give, upon concentration in vacuo and/or lyophilization of the n-butanol layer, Bu-2470A.

Factor Bu-2470A may be purified by ion exchange chromatography with a suitable adsorbent such as DIAION HP-20. As an example, crude Bu-2470A may be applied on a column of DIAION HP-20 and then eluted, successively, with water, aqueous methanol and acidic aqueous methanol. Substantially pure Bu-2470A is generally obtained from the aqueous methanol fractions which may be further purified, if desired, by repetition of the chromatographic procedure.

The Bu-2470B components obtained above may be separated into the individual $B_1$, $B_{2a}$ and $B_{2b}$ components by conventional adsorption procedures. For example, the Bu-2470B mixture may be adsorbed on a column of CM-Cellulose C-25 and the column developed with 0.1 M NaCl. Upon assay, the appropriate fractions are pooled and extracted with n-butanol to give purified Bu-2470$B_1$ and a mixture of Bu-2470$B_{2a}$ and Bu-2470$B_{2b}$. Separation of the $B_{2a}$ and $B_{2b}$ components may be achieved by high performance liquid chromatography (HPLC) using a reversed phase column such as LiChrosorb RP-18.

CHARACTERIZATION OF BU-2470 ANTIBIOTICS

In the description below, component $B_2$ means a mixture of subcomponents $B_{2a}$ and $B_{2b}$ while components $B_1$ and $B_2$ are collectively referred to as Bu-2470B.

Bu-2470A, $B_1$ and $B_2$ are white amorphous solids when isolated as the hydrochloride salts or as the free bases. They may be differentiated from each other and from related octapeptide antibiotics by the TLC and PPC (paper partition chromatography) systems as show in Table 4.

TABLE 4

TLC and PPC of Bu-2470 Components

| | TLC (Rf) PL-111* | BT-101** | PPC (moving distance in cm) PL-1*** |
|---|---|---|---|
| Bu-2470A | 0.01 | 0.09 | 0 |
| Bu-2470$B_1$ | 0.07 | 0.14 | 16.7 |
| Bu-2470$B_2$ | 0.07 | 0.14 | 10.7 |
| EM-49 mixture | 0.11 | 0.17 | 16.7,13.7,10.5 and 6.9 |
| EM-498 | 0.11 | 0.17 | 16.8 |
| 333-25 | 0.07 | 0.14 | 5.6 |
| Bu-1880 | 0.07 | 0.14 | 16.8 |

*PL-111: $CHCl_3$:$C_2H_5OH$:14% $NH_4OH$ (4:7:2v/v)
**BT-101: n-propanol:28% $NH_4OH$:$H_2O$ (8:1:1v/v)
***PL-1: developed with upper layer of n-amyl alcohol:n-amyl acetate:n-propionic acid:$H_2O$ (6:9:5:15v/v) by descending for 16 hours at 27° C.; paper was pre-treated with a 1:1 mixture of acetone and lower phase of the developing solvent system Bu-2470A is readily soluble in water over a wide pH range, aqueous lower alcohols, aqueous dioxane, dimethylsulfoxide and dimethylformamide, slightly soluble in lower alcohols and practically insoluble in other organic solvents. Bu-2470B is soluble in acidic water, aqueous lower alcohols, aqueous dioxane, dimethylsulfoxide and dimethylformamide, slightly soluble in neutral and alkaline water and lower alcohols and insoluble in other organic solvents. Bu-2470A and B give a positive response to ninhydrin reagent but are negative as regards anthrone, Fehling, Sakaguchi and $FeCl_3$ reactions.

The free base and hydrochloride salt of Bu-2740A do not show a definite melting point and decompose above 230° C. Bu-2470 $B_1$ and $B_2$ gradually decompose above 220° C. The microanalytical data and optical rotations for the hydrochlorides of the Bu-2470 components are shown in Table 5.

TABLE 5

Microanalysis and Optical Rotations of Bu-2470 Components

| | | Bu-2470 A | | Bu-2470 $B_1$ | | Bu-2470 $B_2$ | |
|---|---|---|---|---|---|---|---|
| Formula | | $C_{41}H_{71}N_{13}O_8 \cdot 5HCl.4H_2O$ | | $C_{52}H_{91}N_{13}O_{10} \cdot 4HCl.6H_2O$ | | $C_{51}H_{89}N_{13}O_{10} \cdot 4HCl.6H_2O$ | |
| Microanalysis | (Cald'd) | (Found) | (Calc'd) | (Found) | (Calc'd) | (Found) | |
| C: | 43.64 | 42.94 | 47.59 | 47.52 | 47.18 | 46.65 | |
| H: | 7.50 | 7.26 | 8.21 | 7.65 | 8.15 | 7.23 | |
| N: | 16.14 | 16.00 | 13.88 | 13.78 | 14.03 | 13.66 | |
| Cl: | 15.71 | 16.08 | 10.81 | 11.77 | 10.92 | 11.60 | |
| $[\alpha]_D^{29}$ in 0.5N HCl | | −76° | | −53° | | −69° | |

Figure 2:
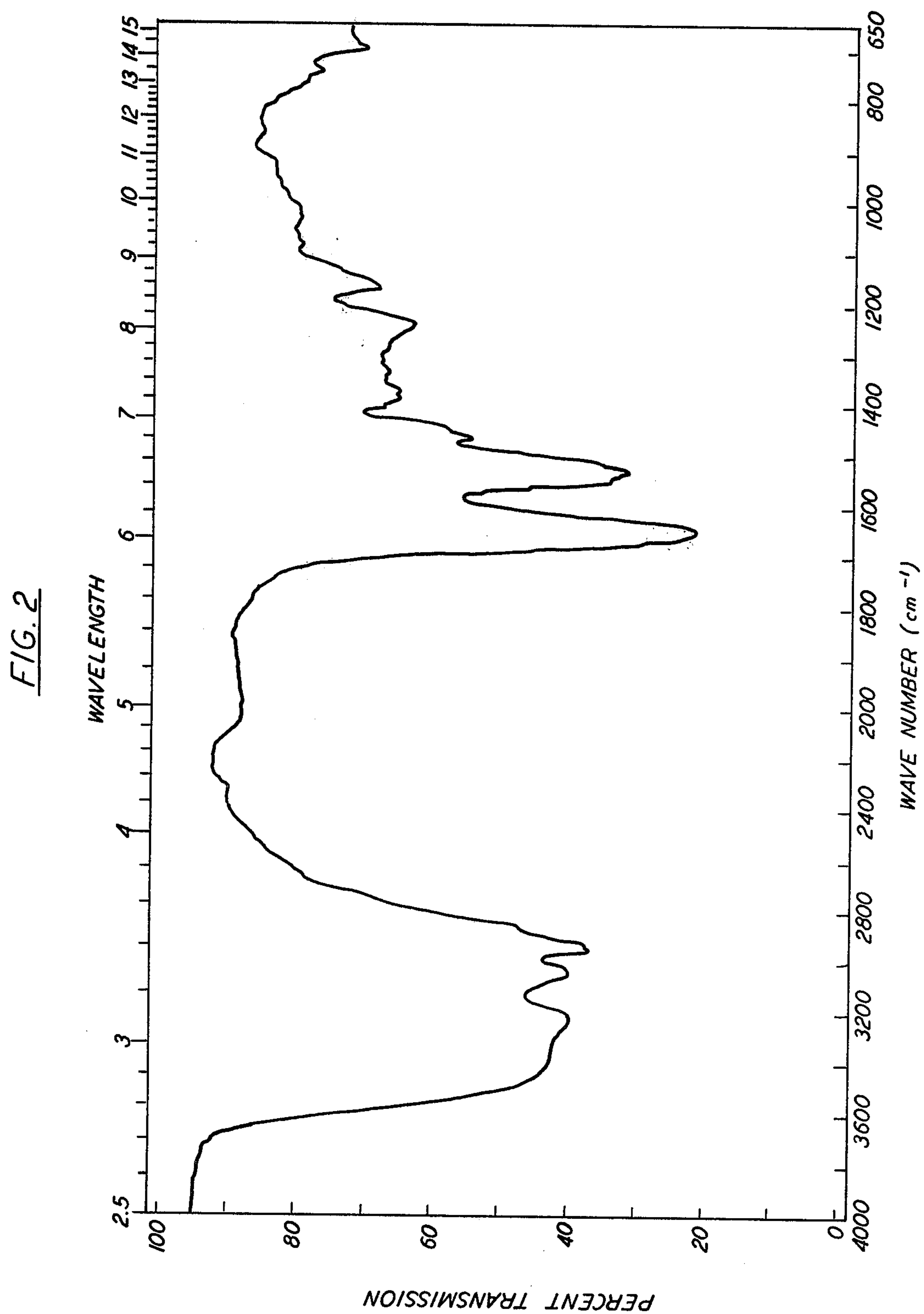
FIG. 2 shows the infrared absorption spectrum of Bu-2470$B_1$ hydrochloride when pelleted in potassium bromide.
Figure 3:
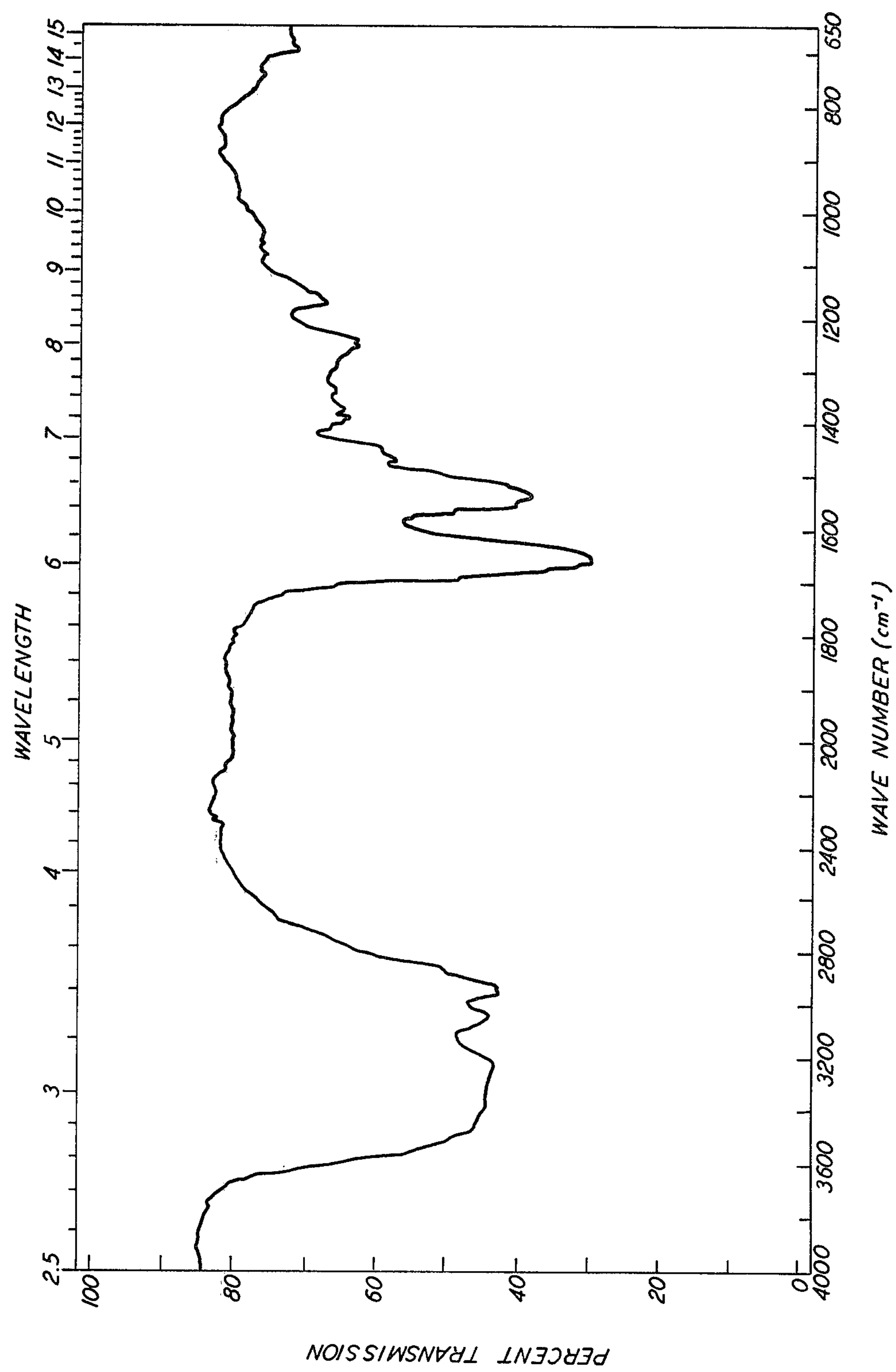
FIG. 3 shows the infrared absorption spectrum of Bu-2470$B_2$ ($B_{2a}+B_{2b}$) hydrochloride when pelleted in potassium bromide.
Figure 4:
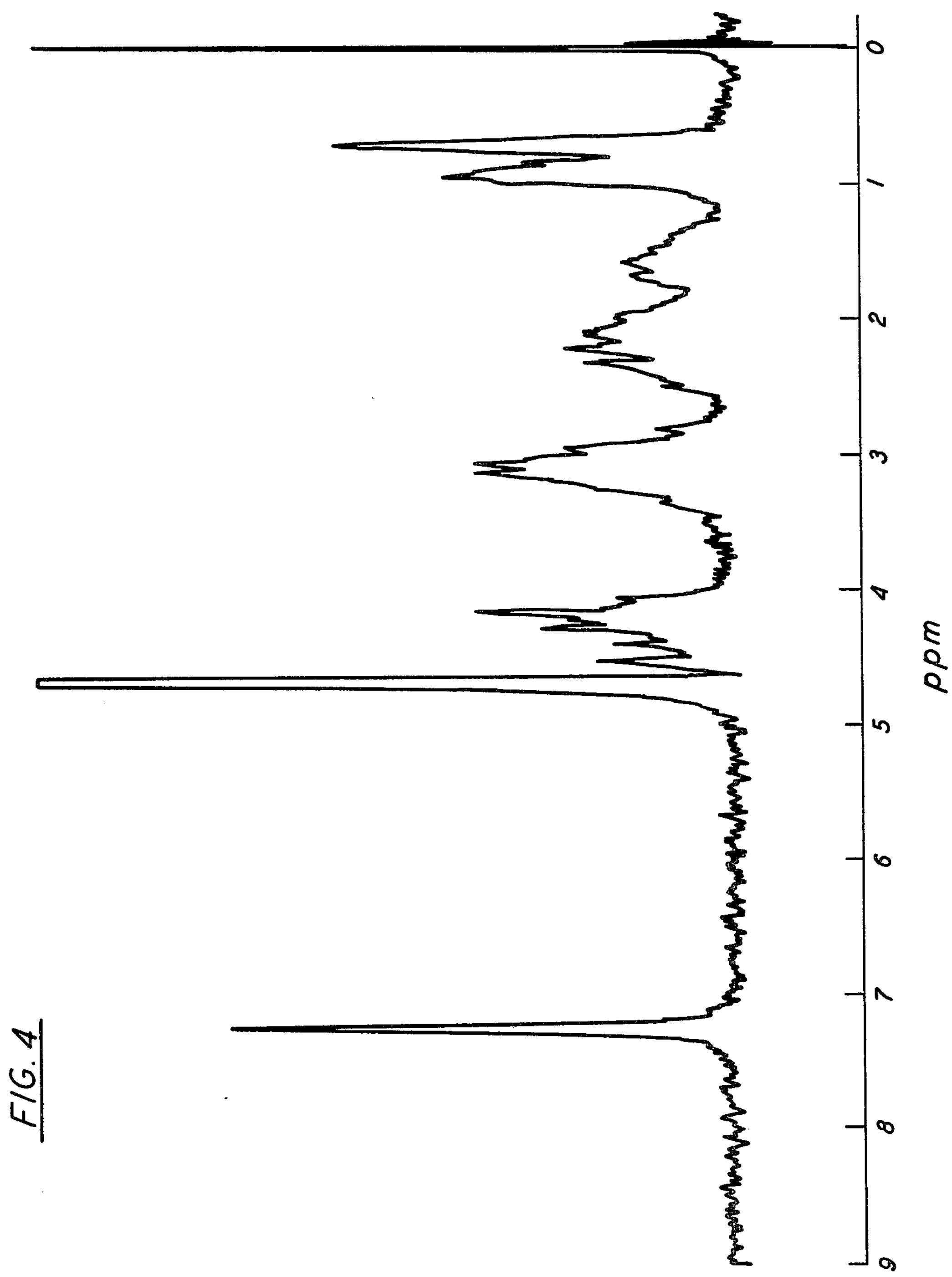
FIG. 4 shows the nuclear magnetic resonance spectrum of Bu-2470A hydrochloride dissolved in $D_2O$ using TMS as the internal reference as determined by a JEOL 60 MHz NMR spectrometer.
Figure 5:
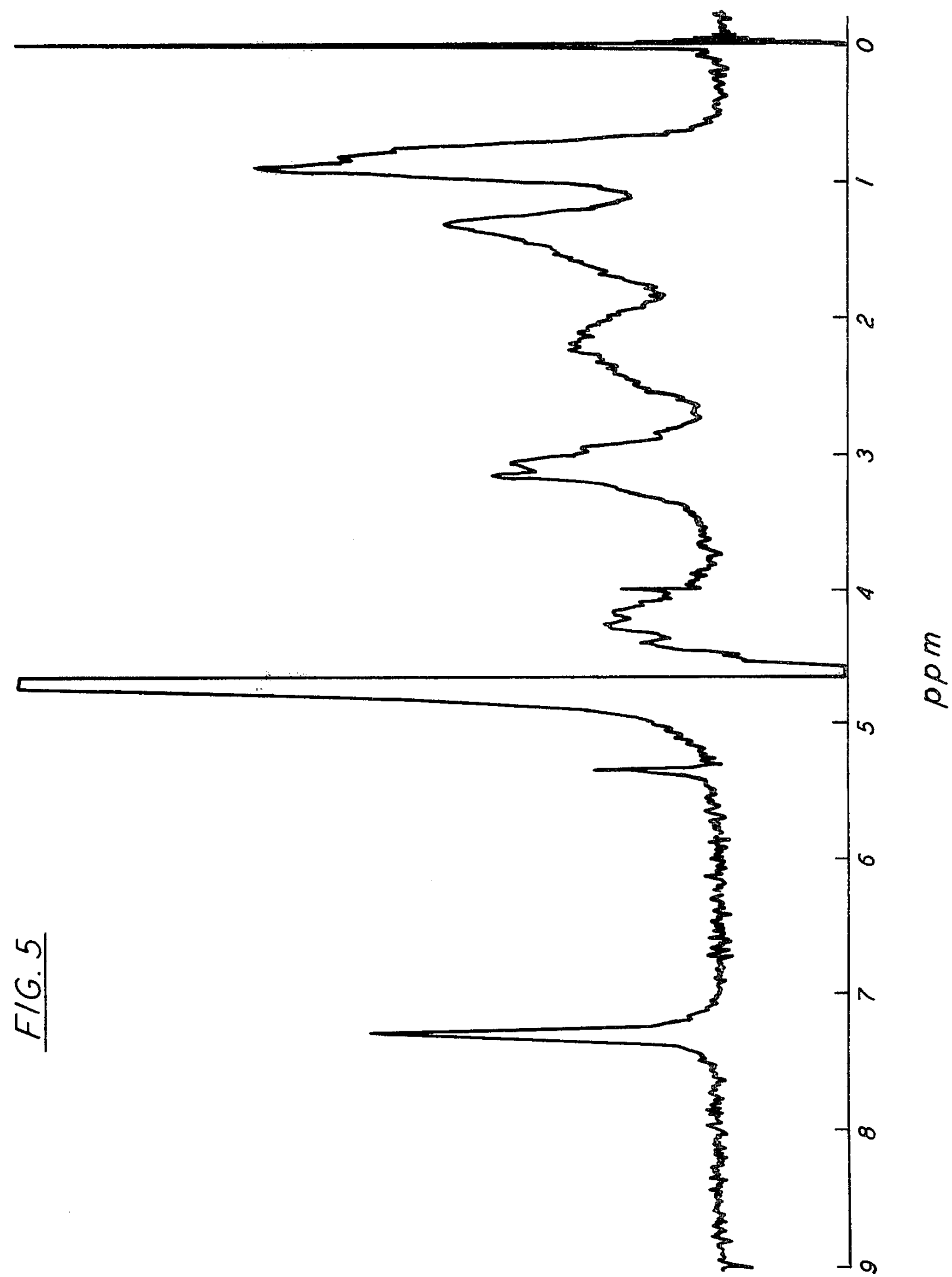
FIG. 5 shows the nuclear magnetic resonance spectrum of Bu-2470$B_1$ hydrochloride dissolved in $D_2O$ using TMS as the internal reference as determined by a JEOL 60 MHz NMR spectrometer.
Figure 6:
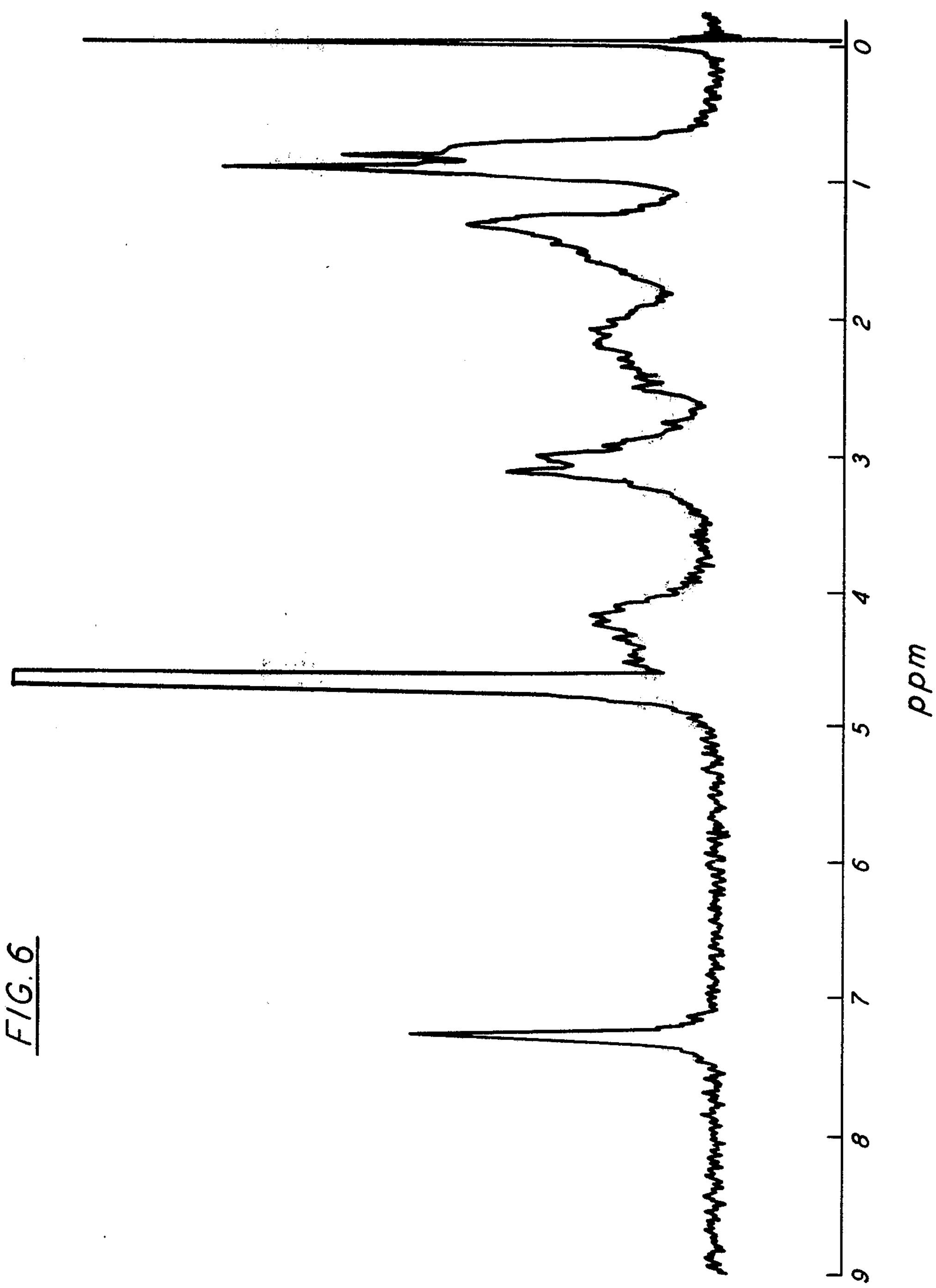
FIG. 6 shows the nuclear magnetic resonance spectrum of Bu-2470$B_2$ ($B_{2a}+B_{2b}$) hydrochloride dissolved in $D_2O$ using TMS as the internal reference as determined by a JEOL 60 MHz NMR spectrometer.

Bu-2470 A and B show only end absorption in the UV spectra. The IR spectra of Bu-2470 A, $B_1$ and $B_2$ are shown in FIGS. 1, 2 and 3, respectively. The proton NMR spectra of Bu-2470 A, $B_1$ and $B_2$ which are presented in FIGS. 4, 5 and 6, respectively, all contain a characteristic five-proton singlet at δ:7.23 ppm, suggesting the presence of a phenyl group in all of the Bu-2470 components.

The structures of Bu-2470 A, $B_1$, $B_{2a}$ and $B_{2b}$ have been determined to be as follows:

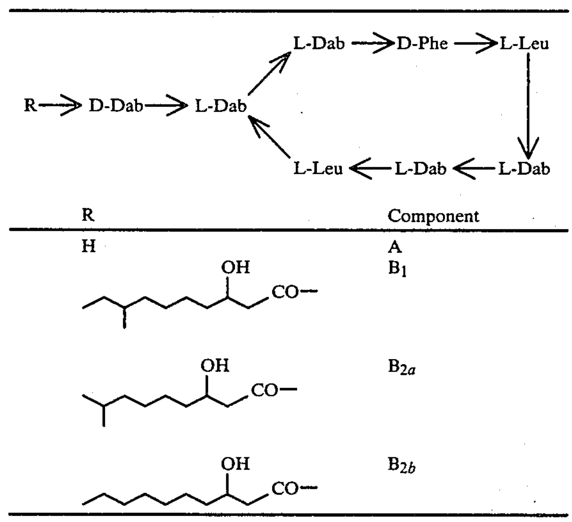

wherein Dab is α,γ-diaminobutyric acid, Leu is leucine and Phe is phenylalanine. The procedures used for structure determination are described below and in Procedures 1–4.

CONSTITUENT AMINO ACIDS

The amino acid analysis of the acid hydrolyzate of Bu-2470A indicated the presence of phenylalanine, leucine and α,γ-diaminobutyric acid with a molar ratio of 1:2:5. The specific rotation values (in 5 N HCl) of the isolated amino acids are +16° for Leu, +5° for Phe and +11° for Dab, indicating that Bu-2470A consists of two L-Leu, one D-Phe and one D- and four L-Dab. No fatty acid was detected in the hydrolyzate.

Bu-2470A was treated with 2,4-dinitroflurobenzene in sodium bicarbonate to afford the penta-N-2,4-dinitrophenyl (DNP) derivative of Bu-2470A. Acid hydrolysis of the DNP derivative in 6 N HCl yielded α,γ-bis-DNP-Dab, γ-DNP-Dab, Dab, Leu and Phe. For identifaction purpose, an authentic sample of bis-DNP-Dab was synthesized by a published method (*J. Am. Chem. Soc.* 76:1328–1331, 1954) and γ-DNP-Dab was obtained from the acid hydrolyzate of DNP-colistin (*J. Chem. Soc.* 1964:4107–4125, 1964). The release of free Dab and bis-DNP-Dab from the DNP-Bu-2470A suggested a cyclic peptide structure with a branched chain, one Dab being at the junction of the peptide ring and the other Dab at the N-terminus of the branched chain. Thus, the amino acid composition, including number and chirality, of Bu-2470A and the location of the two Dab constituents described above are the same as those reported in the literature for antibiotic 333-25.

FATTY ACID MOIETIES

Bu-2470$B_1$ and $B_2$ were heated with 6 N HCl for 16 hours. The amino acid analysis of the hydrolyzate showed that the amino acid constituents of Bu-2470$B_1$ and $B_2$ are the same as those of Bu-2470A. In addition, the presence of a lipophilic acidic substance was indicated in the hydrolyzate of Bu-2470$B_1$ and $B_2$.

Bu-2470$B_1$ was briefly hydrolyzed with 6 N HCl for 30 minutes and the hydrolyzate was extracted with diethyl ether. Evaporation of the ethereal extract afforded a fatty acid which was identified as 3-hydroxy-8-methyldecanoic acid by the GC-MS analysis of its methyl ester. In a similar manner, the hydrolyzate of Bu-2470$B_2$ yielded two fatty acids which were identified as 3-hydroxy-8-methyl-nonanoic acid and 3-hydroxy-n-decanoic acid. Bu-2470$B_2$ was therefore shown to be comprised of two subcomponents having different fatty acid moieties. The two subcomponents were designated as Bu-2470$B_{2a}$ (which contains 3-hydroxy-8-methyl-nonanoic acid) and Bu-2470$B_{2b}$ (which contains 3-hydroxy-n-decanoic acid).

ENZYMATIC DEACYLATION

Kimura and Hiraki in *Bulletin of Mukogawa Women's University* 14: 243–252 (1966) reported that cells of *Pseudomonas* sp. strain M-6-3 possessed an enzymatic activity that deacylates polymyxins. The enzyme was named polymyxin acylase. A strain of *Pseudomonas aeruginosa* K-102 (our strain Pa-74) was found to produce the same type of enzyme capable of deacylating colistin and polymyxin. Although it has been reported to the contrary, polymyxin acylase was found to be capable of deacylating the octapeptin group of antibiotics.

Bu-2470B was suspended in pH7 phosphate buffer and mixed with a preparation of polymyxin acylase. The suspension was incubated at 37° C. with shaking for 3 days. The enzymatic reaction mixture was filtered and extracted with n-butanol at pH 2 to remove unchanged Bu-2470B. The aqueous layer was then made alkaline (pH 9.5) and extracted again with n-butanol. The second butanol extract was evaporated and the residue was purified by chromatography (DIAION HP-20) to afford a bioactive fragment which was identified as Bu-2470A. Enzymatic deacylation of Bu-2470 $B_1$ and $B_2$ gave the same product, Bu-2470A. Thus, Bu-2470 A, $B_1$ and $B_2$ have been shown to have the same octapeptide structure, component A being non-acylated and components $B_1$ and $B_2$ being acylated with different fatty acid moieties.

EM-49 complex and antibiotic 333-25 were also treated with the polymyxin acylase at 37° C. for 5 days affording their deacylation products. Deacyl 333-25 was identified as Bu-2470A by TLC, IR and NMR spectra.

Thus, the peptide structure for each of the Bu-2470 components is identical with that of antibiotic 333-25.

SALT FORMATION

The Bu-2470 antibiotics are basic peptides and thus form salts with organic and inorganic acids. Examples of pharmaceutically acceptable acid addition salts which are included within the scope of the present invention are non-toxic salts with such organic and inorganic acids as hydrochloric, sulfuric, phosporic, acetic, stearic, propionic, tartaric, maleic, benzoic, succinic, and the like. Salt formation is accomplished by conventional methods used with basic antibiotics (such as EM-49), e.g. treatment of the free base with the desired acid followed by lyophilization or solvent precipitation.

BIOLOGICAL PROPERTIES

The antibiotic complex Bu-2470 and the bioactive peptide fractions obtained therefrom have significant antibacterial activity. In in vitro testing, Bu-2470A was generally less active than components $B_1$ and $B_2$ against the organisms tested except for *E. coli* and *Salmonella* species which were about equally susceptible to the three Bu-2470 components. Bu-2470 $B_1$ and $B_2$ ($B_{2a}+B_{2b}$) in in vitro testing showed a broad antibiotic activity against gram-positive and gram-negative bacteria including *Pseudomonas* species, but they did not inhibit *Proteus* species.

Minimal inhibitory concentrations (MIC) of Bu-2470 A, $B_1$ and $B_2$ were determined by a two-fold serial dilution method using Mueller-Hinton agar medium with overnight incubation at 37° C. A $10^{-4}$ dilution of an overnight culture was used as the inoculum. The antibacterial spectra of Bu-2470 A, $B_1$ and $B_2$ are shown in Table 6 below.

TABLE 6

Antibacterial Spectra of Bu-2470A, $B_1$ and $B_2$

| Test Organism | MIC (mcg/ml) Bu-2470A | Bu-2470$B_1$ | Bu-2470$B_2$ |
|---|---|---|---|
| *Staphylococcus aureus* 209P | >100 | 12.5 | 12.5 |
| *Staphylococcus aureus* Smith | >100 | 12.5 | 12.5 |
| *Streptococcus faecalis* B402-3 | 50 | 3.1 | 3.1 |

TABLE 6-continued

Antibacterial Spectra of Bu-2470A, $B_1$ and $B_2$

| Test Organism | MIC (mcg/ml) Bu-2470A | Bu-2470$B_1$ | Bu-2470$B_2$ |
|---|---|---|---|
| *Sarcina lutea* #1001 | 50 | 3.1 | 1.6 |
| *Micrococcus flavus* D-12 | 50 | 3.1 | 3.1 |
| *Bacillus anthracis* IID-115 | 100 | 6.3 | 3.1 |
| *Bacillus subtilis* PCI 219 | 50 | 3.1 | 3.1 |
| *Escherichia coli* NIHJ | 3.1 | 3.1 | 3.1 |
| *Escherichia coli* Juhl | 6.3 | 6.3 | 3.1 |
| *Salmonella enteritidis* #4432 | 12.5 | 6.3 | 3.1 |
| *Salmonella typhosa* A9498 | 6.3 | 6.3 | 3.1 |
| *Shigella dysenteriae* D-163 | 100 | 3.1 | 3.1 |
| *Shigella sonnei* Yale | 25 | 3.1 | 3.1 |
| *Klebsiella pneumoniae* D-11 | 50 | 6.3 | 3.1 |
| *Enterobacter cloacae* A9654 | >100 | 25 | 25 |
| *Proteus mirabilis* A9554 | >100 | >100 | >100 |
| *Proteus vulgalis* A9526 | >100 | >100 | 100 |
| *Proteus morganii* A9553 | >100 | >100 | >100 |

As shown in Table 7, Bu-2470 A, $B_1$ and $B_2$ were active against various *Pseudomonas* species including *P. aeruginosa, P. cepacia, P. maltophilia, P. melanogenum* and *P. putida.* Bu-2470A was shown to be equally or somewhat more active than Bu-2470 $B_1$ and $B_2$ against *Pseudomonas* species.

TABLE 7

Activity Against Pseudomonas Species

| Test organism | MIC (mcg/ml) Bu-2470A | Bu-2470$B_1$ | Bu-2470$B_2$ |
|---|---|---|---|
| *Pseudomonas aeruginosa* D15 | 6.3 | 12.5 | 12.5 |
| *Pseudomonas aeruginosa* A15150 | 12.5 | 12.5 | 6.3 |
| *Pseudomonas aeruginosa* A15194 | 6.3 | 6.3 | 3.1 |
| *Pseudomonas aeruginosa* GN 4925 | 6.3 | 12.5 | 12.5 |
| *Pseudomonas aeruginosa* A21428 | 6.3 | 12.5 | 6.3 |
| *Pseudomonas cepacia* SCH-15 | 50 | 6.3 | 1.6 |
| *Pseudomonas maltophilia* A20620 | 1.6 | 6.3 | 6.3 |
| *Pseudomonas maltophilia* A21384 | 0.4 | 1.6 | 0.8 |
| *Pseudomonas maltophilia* A21550 | 0.8 | 3.1 | 1.6 |
| *Pseudomonas maltophilia* AKH-36 | 0.4 | 0.8 | 1.6 |
| *Pseudomonas maltophilia* AKH-81 | 0.4 | 1.6 | 1.6 |
| *Pseudomonas melanogenum* A20817 | 1.6 | 3.1 | 6.3 |
| *Pseudomonas putida* AKH-15 | 6.3 | 6.3 | 6.3 |
| *Pseudomonas putida* AKH-66 | 12.5 | 6.3 | 3.1 |
| *Pseudomonas putida* KUH-11 | 6.3 | 6.3 | 6.3 |

The in vivo antibacterial activities of Bu-2470 A, $B_1$ and $B_2$ were evaluated in experimental infections of mice caused by *E. coli, K. pneumoniae* and *P. aeruginosa.* Mice were challenged intraperitoneally with a 100 $LD_{50}$ dose of the pathogens in a 5% suspension of hog gastric mucin. Bu-2470 was administered by the intramuscular route immediately after the bacterial challenge. A group of 5 mice was used for each dosage level with animals being observed for 5 days to determine the median protective dose ($PD_{50}$). The results are shown in Table 8. Bu-2470A was found to be relatively more active in vivo than in vitro in comparison with components $B_1$ and $B_2$.

TABLE 8

In Vivo Activity of Bu-2470

| Challenge organism | $PD_{50}$ (mg/kg, im) Bu-2470A | Bu-2470$B_1$ | Bu-2470$B_2$ |
|---|---|---|---|
| *E. coli* Juhl | 7.6 | 50 | — |
| *K. pneumoniae* A9977 | 25 | 43 | — |
| *P. aeruginosa* A9843 | 25 | 100 | 22 |

The acute toxicities of Bu-2470 A and $B_1$ were determined in mice by intravenous(iv) and subcutaneous (sc) routes. Colistin was tested comparatively as a reference compound. As shown in Table 9, Bu-2470$B_1$ was less toxic than colistin by both iv and sc routes, while Bu-2470A was less toxic than colistin by the iv route but more toxic by the sc route.

TABLE 9

| Route of Administration | Acute Toxicity of Bu-2470 $LD_{50}$ (mg/kg) Bu-2470A | Bu-2470$B_1$ | Colistin |
|---|---|---|---|
| intravenous | 35 | 35 | 8.8 |
| subcutaneous | 56 | 280 | 115 |

As indicated by the in vivo and in vitro screening data discussed above, Bu-2470 and its bioactive components Bu-2470 A, $B_1$, $B_{2a}$ and $B_{2b}$ are useful as antibacterial agents, as nutritional supplements in animal feeds and as therapeutic agents in poultry and animals, including man. They are especially valuable in the treatment of infectious diseases in animals (particularly poultry and mammals) caused by gram-positive and gram-negative bacteria sensitive to the Bu-2470 antibiotics.

The invention includes within its scope pharmaceutical compositions containing an effective antibacterial amount of Bu-2470 A, $B_1$, $B_{2a}$ or $B_{2b}$, (including pharmaceutically acceptable acid addition salts thereof), or a mixture thereof, in combination with an inert pharmaceutically acceptable carrier or diluent. Such compositions may be made up in any pharmaceutical form appropriate for the route of administration in question. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. Parenteral compositions may also be manufactured in the form of sterile solid compositions which can be dissolved in sterile water, physiological saline or some other sterile injectable medium immediately before use.

The antibiotics of the present invention (including pharmaceutically acceptable acid addition salts thereof) are administered so that the concentration of antibiotic is greater than the minimum inhibitory concentration for the particular organism being treated. It will of course be appreciated that the actual dose of antibiotic used will be determined by the physician or veterinarian after consideration of such factors as age, body weight, sex, diet, route of administration, rate of excretion, condition of the patient, drug combinations and the particular situs and disease being treated.

The present invention also provides a method for therapeutically treating an animal host (particularly poultry and mammals including man) affected by a gram-positive or gram-negative bacteria which comprises administering to said host an effective antibacterial dose of Bu-2470 (including the individual components of Bu-2470 A, $B_1$, $B_{2a}$ or $B_{2b}$ or mixtures thereof) or a pharmaceutically acceptable acid addition salt thereof.

The following examples are provided for illustrative purposes only and are not intended to limit the scope of the invention. AMBERLITE IRC-50 (trademark of Rohm and Haas Co., Philadelphia, Pa.) is a weakly acidic cation exchange resin of a carboxylic-polymethacrylic type. AMBERLITE IR-45 (trademark of Rohm and Haas Co.) is a weakly basic anion exchange resin. DIAION HP-20 (trademark of Mitsubishi Chemical Industries, Japan) is a nonionic macroreticular (macroporous) polymer resin. DOWEX 50W (trademark of Dow Chemical Co., U.S.A.) is a strongly acidic cation exchange resin having a sulfonic acid functionality. LiChrosorb (trademark of E. Merck) RP-18 is a microparticulate HPLC column packing.

STRUCTURE DETERMINATION EXPERIMENTS

Procedure 1—Hydrolysis of Bu-2470A

A solution of Bu-2470A (300 mg) in 15 ml of 6 N HCl was heated at 105° C. for 15 hours in a sealed tube. The reaction mixture was concentrated in vacuo to dryness. The residue was dissolved in 1 ml of water and chromatographed on a column of DOWEX 50W×4 (12×250 mm). The column was developed with increasing concentration of hydrochloric acid (0.1 N–1.0 N), the elution being monitored by ninhydrin test and TLC*. The appropriate fractions were collected and concentrated in vacuo to yield the following three amino acids:

| | Leucine (Leu) | Phenylalanine (Phe) | α,γ-Diaminobutyric acid (Dab) |
|---|---|---|---|
| Eluted with | 0.3N HCl | 0.5N HCl | 1N HCl |
| Yield | 78 mg | 45 mg | 237 mg |
| TLC (silica gel plate) | | | |
| system A* | 0.47 | 0.59 | 0.02 |
| system B** | 0.35 | 0.37 | 0.07 |
| $[\alpha]_D^{28.5}$ (c 1.0,5N HCl) | +15° | +5° | +11° |
| Chirality assigned | L | D | 1D + 4L |

*phenol:$H_2O$ (4:1 v/v)
**n-butanol:acetic acid:$H_2O$ (12:3:5 v/v)

Procedure 2—Preparation and Acid Hydrolysis of Penta(2,4-dinitrophenyl)-Bu-2470A A solution of dinitrofluorobenzene (236 mg) in 2 ml of ethanol was added to an aqueous solution (4 ml) of Bu-2470A (100 mg) and $NaHCO_3$ (134 mg), and the mixture was stirred for 1.5 hours at 20° C. in a dark room. The yellow solid which precipitated was collected by filtration, washed with water and benzene, and then dried in vacuo. The crude product was purified by silica gel chromatography. The column (10×200 mm) was eluted with $CHCl_3$:$CH_3OH$(93:7) and the elution was monitored by the characteristic yellow color and TLC. The appropriate fractions were collected and evaporated in vacuo to give 111 mg of the DNP derivative of Bu-2470A, $\lambda_{max}$ in 5% dioxane-$CH_3OH$:347 nm ($E_{1\,cm}^{1\%}$ 472). TLC (SD-105)*:Rf 0.43.

*$CHCl_3$:$CHCO_3$ (9:1 v/v)

A sample of DNP-Bu-2470A (5 mg) was heated at 105° C. with 0.5 ml of 6 N HCl in a sealed tube for 15 hours. The reaction mixture was concentrated in vacuo and lyophilized. The yellow solid thus obtained was analyzed by TLC and the following five compounds were identified:

| | TLC (Rf) System PL-111** | Detection |
|---|---|---|
| α,γ-bis-DNP—Dab | 0.63 | yellow color |
| γ-DNP—Dab | 0.45 | yellow color |
| Phe | 0.41 | ninhydrin |
| Leu | 0.38 | ninhydrin |

-continued

| | TLC (Rf) System PL-111** | Detection |
|---|---|---|
| Dab | 0.06 | ninhydrin |

**$CHCl_3$:$C_2H_5OH$:14% $NH_4OH$ (4:7:2v/v)

Procedure 3—Isolation of Fatty Acids From Bu-2470B$_1$ and B$_2$, Bu-1880 and EM-49

A solution of Bu-2470B$_1$ (10 mg) in 0.5 ml of 6 N HCl was heated at 105° C. for 0.5 hours in a sealed tube. The hydrolyzate was added with 5 ml of water and extracted with two 5 ml portions of diethyl ether. The ethereal solution was dried over anhydrous $Na_2SO_4$ and concentrated in vacuo to give an oily residue (2 mg). The oil was taken into 3 ml of ether and treated with an excess of diazomethane in ethereal solution. Evaporation of the solvent gave the methyl ester (2 mg) which was analyzed by GC and GC-MS (gas chromatography and gas chromatography-mass spectrometry).

In the same manner, Bu-2470B$_2$ (10 mg), Bu-1880 (10 mg) and EM-49 (10 mg) were hydrolyzed and the fatty acid moieties converted to methyl esters. The GC and GC-MS analysis of these methyl esters are shown below:

| Fatty acid methyl esters isolated from | GC* (rt. in minutes) | GC—MS** (m/e) | | | |
|---|---|---|---|---|---|
| | | $M^+$ | base peak | diagnostic peaks | identifaction |
| Bu-2470B$_1$ | 5.77 | 216 | 103 | 199,167, 57 | Methyl 3-hydroxy-8-methydecanoate |
| Bu-2470B$_2$ | 4.28 | 202 | 103 | 185,137, 109,107 | Methyl 3-hydroxy-8-methylnonanoate |
| | 4.80 | 202 | 103 | 185,127, 110 | Methyl 3-hydroxy-n-decanoate |
| Bu-1880 | 5.79 | 216 | 103 | 199,167, 57 | Methyl 3-hydroxy-8-methyldecanoate |
| EM-49 complex | 4.27 | 202 | 103 | 185,137, 109,107 | Methyl 3-hydroxy-8-methylnonanoate |
| | 4.79 | 202 | 103 | 185,127, 110 | Methyl 3-hydroxy-n-decanoate |
| | 5.77 | 216 | 103 | 199,167, 57 | Methyl 3-hydroxy-8-methyldecanoate |

*OV-17 3%, He, Temp. programming 5° C./min from 140° C.
**OV-17 1.5%, He, Temp. programming 5° C./min from 140° C.

Procedure 4—Isolation of Deacyl Bu-2470B, deacyl EM-49 and deacyl 333-25

A suspension of Bu-2470B (100 mg) in 30 ml of 1/15 M Sörensen's phosphate buffer (pH 7.0) was combined with polymyxin acylase (120 mg) and the mixture incubated at 37° C. with shaking for 3 days. The enzymatic reaction mixture was centrifuged and the clear supernatant adjusted to pH 2.0 and extracted with two 20 ml portions of n-butanol. Evaporation of the extract yielded 26 mg of unchanged Bu-2470B. The aqueous layer was adjusted to pH 9.5 with 2 N $NH_4OH$ and extracted again with two 20 ml aliquots of n-butanol. Second butanol extracts were combined and concentrated in vacuo to afford the crude solid of deacyl Bu-2470B (55 mg). The solid was dissolved in 2 ml of water, adjusted to pH 2.0 with 1 N HCl and chromatographed on a column of DIAION HP-20 (10×160 mm). The column was developed with water and the fractions were monitored by ninhydrin assay and TLC*. The yield of deacyl Bu-2470B was 32 mg.

*$SiO_2$,$CHCl_3$:$CH_3OH$:28% $NH_4OH$ (1:2:1 v/v)

By essentially the same procedure as described in the above experiment, EM-49 complex (10 mg) was treated with polymyxin acylase (12 mg) affording 5.0 mg of deacyl EM-49 along with 1.5 mg of EM-49 recovered. Similarly, deacylation of antibiotic 333-25 (10 mg) with polymyxin acylase (12 mg) yielded 4.9 mg of deacyl 333-25 and 2.5 mg of unchanged 333-25.

EXAMPLE 1

Fermentation of Bu-2470 Complex

An agar slant of *Bacillus circulans* strain G493-B6 with well-established growth was used to inoculate vegetative medium containing 2% glycerol, 1% corn steep liquor, 1% PHARMAMEDIA (trademark for cottonseed meal), 0.3% $(NH_4)_2SO_4$, 0.003% $ZnSO_4.7H_2O$ and 0.4% $CaCO_3$, the pH being adjusted to 7.0 before sterilization. The second culture was incubated at 28° C. for 72 hours on a rotary shaker (250 rpm), and 5 ml of the culture was transferred to a 500 ml Erlenmeyer flask containing 100 ml of fermentation medium composed of 3% glycerol, 3% soybean meal, 0.3% $(NH_4)_2SO_4$, 0.003% $ZnSO_4.7H_2O$ and 0.4% $CaCO_3$ (pH 7.0). The fermentation was carried out on a rotary shaker at 28° C. for 5 to 7 days. Antibiotic activity in the fermentation broth was determined by paper disc-agar diffusion assay using *Bacillus subtilis* PCI 219 and *Escherichia coli* NIHJ as the test organisms. Antibiotic production reached a maximum on the sixth day at a time when the fermentation broth generally became viscous. The antibiotic concentration was approximately 1000 mcg/ml.

EXAMPLE 2

Recovery of the Bu-2470 Components

The viscous fermentation broth from Example 1 (10 L, pH 7.5) was diluted to 25 L with water and a small amount of antifoam. The mycelial cake was removed by continuous centrifuge and the clear broth supernatant was stirred with AMBERLITE IRC-50 ($NH_4^+$,2 L). The resin was washed with water (20 L) and then eluted with three 2.5 L portions of 0.5 N HCl to liberate the antibiotic activity. The active eluates were combined (9 L), adjusted to pH 7.0 and stirred with active charcoal (180 g). The carbon was separated and the activity adsorbed was eluted twice with a mixture of n-butanol and water (1:1 v/v, 2 L), the pH of the eluant being adjusted to 2.0 with 6 N HCl. The n-butanol layer (1.5 L) was separated and concentrated in vacuo to yield a crude mixture of Bu-2470B components (B$_1$, B$_{2a}$ and B$_{2b}$) (1.35 g). The acidic aqueous layer was neutralized with AMBERLITE IR-45 (OH—) and extracted with two 1 L portions of n-butanol. Evaporation of the n-butanol extract afforded an additional amount of Bu-2470B mixture (440 mg). The aqueous layer was then made alkaline (pH 10.0) with concentrated $NH_4OH$ and extracted again with n-butanol (1 L×3). The latter n-butanol extracts were combined, concentrated in vacuo and lyophilized to afford a crude solid of Bu-2470A (4.65 g).

The crude preparation of Bu-2470A (5.5 g) was applied on a column of DIAION HP-20 (800 ml, washed with 0.1 N $NH_4OH$ before use) which was successively developed with water (3.5 L), 50% methanol (5.5 L) and acidic 50% methanol (pH 2, 3.5 L). The elution was monitored by bioassay (vs. Pseudomonas strain Pss-1) and TLC (thin layer chromatography) (silica gel plate, $CHCl_3$:$CH_3OH$:28% $NH_4OH$ 1:2:1 v/v). The bioactive fractions eluted first with 50% methanol were pooled and concentrated to give a pure preparation of Bu-2470A (788 mg). Subsequent active fractions contained a trace of impurities and were further purified by repetition of the same chromatography to afford an additional amount of pure Bu-2470A (1.0 g).

The crude sample of component B mixture (500 mg) was loaded on a column of CM-Cellulose C-25 (400 ml., pretreated with 0.1 M NaCl). The column was developed with 0.1 M NaCl and the eluates were examined by bioassay against *B. subtilis* PCI-219. The appropriate fractions were pooled and extracted with n-butanol. Bu-2470$B_2$ (75 mg) was eluted first followed by a mixture of Bu-2470$B_1$ and $B_2$ (89 mg) and then pure Bu-2470$B_1$ (89 mg). Bu-2470$B_2$ was later determined to be a mixture of two subcomponents, Bu-2470$B_{2a}$ and Bu-2470$B_{2b}$.

EXAMPLE 3

Separation of Bu-2470 $B_2$ Subcomponents

The $B_2$ component of Bu-2470 was further separated into two subcomponents Bu-2470 $B_{2a}$ and Bu-2470 $B_{2b}$ by HPLC technique using Waters Associates Inc. Model 6000A apparatus (with U6K injector and 440 UV detector) and a reversed phase column (LiChrosorb RP-18, $\Phi 4 \times 30$ mm). The chromatograph was carried out at a flow rate of 1.0 ml/min. and an inlet pressure of 2500 psi. The mobile phase was a mixture of acetonitrile and 0.005 M tartarate buffer in a ratio of 36:64 v/v, the buffer solution being supplemented with sodium sulfate (0.05 M) and sodium heptanoate (0.005 M). The elution was monitored by UV absorption at 254 nm. Bu-2470 $B_{2a}$ was eluted first with a retention time ($R_t$) of 7.42 minutes followed by Bu-2470 $B_{2b}$ at $R_t$ 8.17 min. Bu-2470 $B_1$ appeared at $R_t$ 12.42 min. under the same conditions.

We claim:

1. A peptide antibiotic compound of the formula

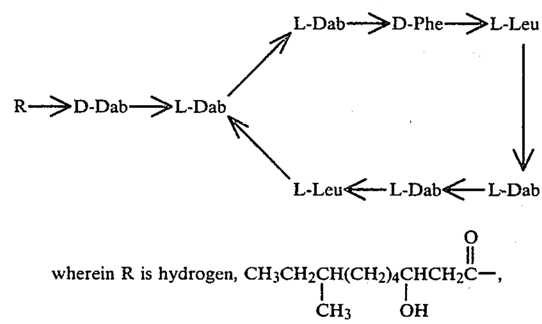

wherein R is hydrogen, $CH_3CH_2CH(CH_3)(CH_2)_4CH(OH)CH_2C(=O)-$,

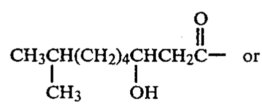

$CH_3CH(CH_3)(CH_2)_4CH(OH)CH_2C(=O)-$ or

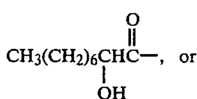

$CH_3(CH_2)_6CH(OH)C(=O)-$, or a pharmaceutically acceptable acid addition salt thereof, wherein Dab represents $\alpha,\gamma$-diaminobutyric acid, Leu represents leucine and Phe represents phenylalanine.

2. The peptide antibiotic Bu-2470A of the formula

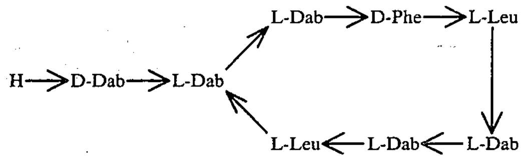

or a pharmaceutically acceptable acid addition salt thereof, wherein Dab represents $\alpha,\gamma$-diaminobutyric acid, Leu represents leucine and Phe represents phenylaline.

3. The peptide antibiotic Bu-2470A of claim 2 in its free base form.

4. The hydrochloric acid salt of the peptide antibiotic Bu-2470A of claim 2.

5. The peptide antibiotic Bu-2470$B_1$ of the formula

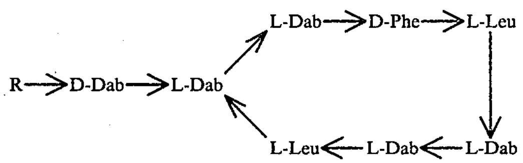

wherein R is

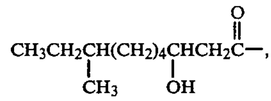

$CH_3CH_2CH(CH_3)(CH_2)_4CH(OH)CH_2C(=O)-$,

Dab represents $\alpha,\gamma$-diaminobutyric acid, Leu represents leucine and Phe represents phenylalanine, or a pharmaceutically acceptable acid addition salt thereof.

6. The peptide antibiotic Bu-2470$B_1$ of claim 5 in its free base form.

7. The hydrochloric acid salt of the peptide antibiotic Bu-2470$B_1$ of claim 5.

8. The peptide antibiotic Bu-2470$B_{2a}$ of the formula

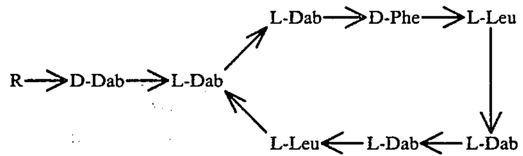

wherein R is

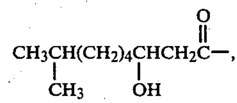

$CH_3CH(CH_3)(CH_2)_4CH(OH)CH_2C(=O)-$,

Dab represents $\alpha,\gamma$-diaminobutyric acid, Leu represents leucine and Phe represents phenylalanine, or a pharmaceutically acceptable acid addition salt thereof.

9. The peptide antibiotic Bu-2470$B_{2a}$ of claim 8 in its free base form.

10. The hydrochloric acid salt of the peptide antibiotic Bu-2470$B_{2a}$ of claim 8.

11. The peptide antibiotic Bu-2470$B_{2b}$ of the formula

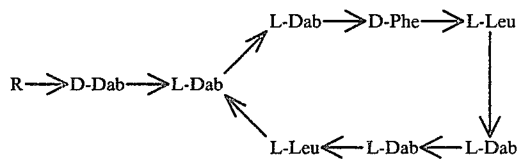

wherein R is

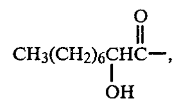

Dab represents $\alpha,\gamma$-diaminobutyric acid, Leu represents leucine and Phe represents phenylalanine, or a pharmaceutically acceptable acid addition salt thereof.

12. The peptide antibiotic Bu-2470$B_{2b}$ of claim 11 in its free base form.

13. The hydrochloric acid salt of the peptide antibiotic Bu-2470$B_{2b}$ of claim 11.

14. An antibacterial pharmaceutical composition comprising an effective antibacterial amount of at least one antibiotic peptide as claimed in claim 1, in combination with an inert pharmaceutically acceptable carrier or diluent.

* * * * *